United States Patent [19]
Cerqueira et al.

[11] Patent Number: 5,925,357
[45] Date of Patent: Jul. 20, 1999

[54] BIFURCATED METHOD TO PROCESS ALOE WHOLE LEAF

[75] Inventors: Luiz Cerqueira, Irving, Tex.; L. Scott McKnight, Irving, Tex.; Santiago Rodriguez, Miami, Fla.; Carlton E. Turner, Irving, Tex.

[73] Assignee: Carrington Laboratories, Inc., Irving, Tex.

[21] Appl. No.: 08/818,962

[22] Filed: Mar. 14, 1997

[51] Int. Cl.⁶ .............................. A01N 65/00; A23L 1/05
[52] U.S. Cl. ..................... 424/195.1; 426/518; 426/519; 426/521; 426/573
[58] Field of Search .................... 424/195.1; 426/63, 426/518, 519, 521, 534, 573

[56] References Cited

U.S. PATENT DOCUMENTS

| | | | |
|---|---|---|---|
| 4,735,935 | 4/1988 | McAnalley | 514/53 |
| 4,917,890 | 4/1990 | McAnalley | 424/195.1 |
| 5,356,811 | 10/1994 | Coats | 435/267 |

FOREIGN PATENT DOCUMENTS 81-65247  6/1996  Japan .

OTHER PUBLICATIONS

Norton S.J., Talesa V., Yuan W.J., and Principato G.B., "Glyozalase I and Glyoxalase II from Aloe Vera: Purification, Characterization and Comparison with Animal Glyoxalases," Biochemistry International, vol. 22, No. 3, Nov. 1990, pp. 411–418.

F. Sabeh, T. Wright, and S.J. Norton, "Isozymes of Superoxide Dismutase from Aloe Vera," 29th Meeting of the European Metabolic Group, London, Jun. 13–16, 1996, pp. 212–221.

*Primary Examiner*—Sandra E. Saucier
*Attorney, Agent, or Firm*—Hitt Chwang & Gaines P.C.

[57] ABSTRACT

A bifurcated method to process an aloe whole leaf by processing the aloe fillet and the aloe rind separately and subsequently combine the products from these separate processes, and the use of the final combined product.

22 Claims, 1 Drawing Sheet

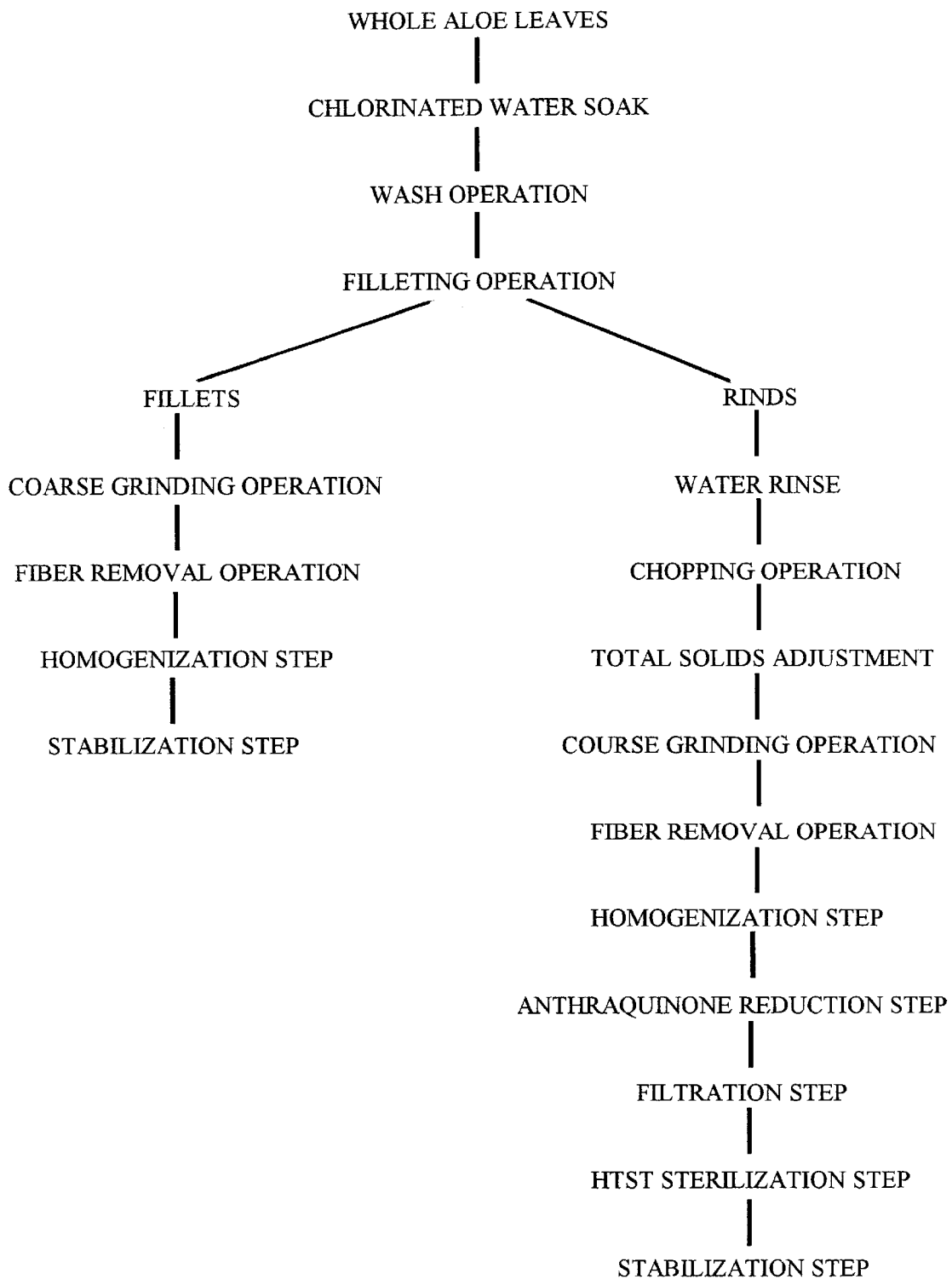

BIFURCATED METHOD TO PROCESS ALOE WHOLE LEAF

BACKGROUND

The present invention relates to a bifurcated method to process an aloe whole leaf. More specifically, the present invention relates to a method to process an aloe whole leaf by processing the aloe fillet and the aloe rind separately and subsequently combine the products from these separate processes, and the use of the final combined product Aloe is a tropical or subtropical plant characterized by lance-shaped leaves with jagged edges and sharp points.

When an aloe vera leaf is sliced transversely, it will reveal the outer walls of the epidermis covered with thick cuticles. Beneath the epidermis is the mesophyll which is differentiated into chlorenchyma cells and thinner walled cells known as parenchyma. The parenchyma cells harbor a transparent mucilaginous jelly. The vascular bundles with inner bundle sheath cells contain the yellow sap having laxative properties and are sandwiched between the two major cells. Aloe vera contains two major liquid sources, a yellow latex (exudate) and the clear gel (mucilage). The mucilaginous jelly from the parenchyma cells of the plant is referred to as aloe vera gel. Thus, there are broadly three distinct portions of the aloe vera leave: (1) Yellow sap, mainly anthraquinones; (2) internal gel matrix or the "fillet"; and (3) the "rind" which consists of outer rinds, tips, bases and thorns.

Whole leaves, exudates and fresh gels of aloe plants have been used for a variety of human afflictions. For centuries, the aloe vera plant has been considered to have, and has been used for its, medicinal and therapeutic properties without any clear understanding or scientific analysis of the bases for such properties. Further, it is known that the biological activities of fresh aloe plant decay very rapidly.

Because of this lack of knowledge about the aloe plant and its characteristics, most methods employed for the processing of the plant result in end products which do not consistently achieve desired results. Further, aloe leaves contain anthraquinones in its yellow sap. The anthraquinone-containing yellow sap is known to have a laxative effect with a reputation as an extremely irritating cathartic.

Traditionally, people have either processed the whole aloe leaf or processed only the fillet and discarded the rind. It is believed, however, that both the aloe fillet and the aloe rind contain bioactive materials. Thus, by discarding the rind, one may be discarding some bioactive materials from the whole leaf of the aloe vera.

Traditional "whole-leaf" processes for the production of various aloe products typically involved crushing (pressure rollers), grinding (e.g., use of Thompson aloe leaf slitter), or pressing (TCX pressure extruder) of the entire leaf of the aloe plant to produce an aloe vera juice, followed by various steps of filtration and stabilization of the juice. The resulting mixture is then incorporated in, or mixed with, other solutions or agents to produce the products which could be, for example, a cosmetic, a health food drink, or a topical ointment.

Typically, in a "whole-leaf" process for the production of aloe product suitable for making beverages is to crush and grind a washed aloe whole leaf to obtain the thick liquid. In this process, the rind is not separated from the fillet of the aloe leaf. The cellulose fibers are then removed by filtration. Then an enzyme, such as a cellulase or mannosidase, is added to the stabilized aloe liquid to "digest" the cellulose. This "digestion" step is necessary to reduce the very high viscosity that the liquid bears. High viscosity, or thick, liquid tends to leave an unpleasant feeling in the mouth. Then charcoal is added to the "digested" aloe liquid to decolorize the liquid and to remove aloin and anthraquinones that have laxative effects. The charcoal is then removed by filtration. The filtered aloe liquid is then pasteurized at high temperature. The remaining aloe liquid, obtained from the leaf in its entirety, is then stabilized with a preservative, such as sodium benzoate, potassium sorbate, Vitamin E, hydrogen peroxide, sodium sulfite, sodium bisulfite, or others. The resultant liquid is then concentrated to reduce the amount of water. Alternatively, almost all of the water is removed to yield a powder.

Unfortunately, because of improper processing procedures, many of these so-called aloe products contain very little or no bioactive chemical substances or ingredients. In a typical "whole-leaf" process, the rind and the fillet of the aloe leaf are processed together, and the resultant liquid is subjected to a number of steps that are detrimental to many of the bioactive chemical substances naturally present in the fillet of the leaf. For example, either one of the "enzymatic digestion," the charcoal treatment, and the pasteurization can destroy or eliminate the naturally occurring bioactive chemical substances or ingredients present in the fillet of the aloe leaf.

The principal disadvantage of such state of the art processes is the failure to recognize, and to take into account, that different fractions and components of the aloe leaf have different kinds of biological activities. These different fractions have characteristics that may not only be inconsistent with the intended use of the final product, but in many instances were deleterious to such use. Further, unless carefully controlled processes are used in processing the leaves of the aloe plant, the active chemical substances, or ingredients, of the leaves are destroyed during the process.

Aloe vera leaves contain a variety of chemical substances and components. Mixtures of active chemical substances of aloe leaves have been identified, isolated and stabilized as described in U.S. Pat. Nos. 4,735,935, 4,851,224, 4,917,890, 4,957,907, 4,959,214, and 4,966,892, the content of each of these is incorporated herein by reference. One group of the active chemical substances has been referred to as aloe vera mucilaginous polysaccharides. Even the aloe vera mucilaginous polysaccharides are made up of a mixture of polysaccharides. The term "polysaccharides" has been used loosely to include both oligomers and polymers of carbohydrates. A group of such polysaccharides has been given the name acemannan. Acemannan is an ordered linear polymer of substantially acetylated mannose monomers.

The biological, or physiological, activities of aloe vera mucilaginous polysaccharides and their pharmaceutical applications have been the object of numerous research studies at a number of laboratories, including Carrington Laboratories. Uses of aloe products have been described in U.S. Patent Nos. Carrington's U.S. Pat. Nos. 5,106,616, 5,118,673, 5,308,838, 5,409,703, 5,441,943, and 5,443,830, each assigned to Carrington Laboratories, Inc., the content of each of which is incorporated by reference herein. These studies have primarily focused on the activities of bioactive chemical substances of aloe vera as antiviral agents, antitumor agents, immunostimulants, immunomodulators, vaccine adjuvants, means of reducing opportunistic infections, means of controlling inflammation, and means of stimulating the wound healing processes.

Aloe vera mucilaginous polysaccharides have been shown in controlled studies to increase the rate of healing in animals. Aloe vera mucilaginous polysaccharides have also been shown to be an effective treatment for gastric ulcers in animal studies.

Acemannan, for example, has been shown in laboratory studies to increase up to 300% in 48 hours the replication of fibroblasts in tissue culture which are known to be responsible for healing burns, ulcers and other wounds of the skin and of the gastrointestinal lining.

Over a three year period, laboratory rats, the stomachs of which react similarly to that of humans, were tested. Acemannan was found to be equivalent to or superior to current medications used for the treatment of gastric ulcers. Most such products act to inhibit hydrochloric acid in the stomach. Acemannan works on a different principle and does not alter the natural flow of digestive acids.

In view of the known wide spectrum of biological activities possessed by leaves of aloe plant, and in view of the known complex mixtures of biologically active components and substances found in the leaves of aloe plant, it is desirable to be able to process an aloe whole leaf with the aim of retaining essentially every bioactive component of the aloe vera leaf. A need has arisen for a simple and effective method to process the aloe vera whole leaf and whose process preserves and maintains almost all of the bioactive chemical entities naturally present in the aloe whole leaf.

SUMMARY

The problems discussed above have been solved in the present invention which provides for a bifurcated method to process the aloe whole, their products and uses.

Broadly, the present bifurcated method to process an aloe whole leaf comprises the steps of:
(a) separating rind and fillet from a cleaned aloe whole leaf;
(b) subjecting the fillet to the steps of:
  (i) squeezing to give a crude fillet liquid;
  (ii) removing coarse fibers from the crude fillet liquid to give a fillet liquid;
  (iii) stabilizing the fillet liquid with a preservative to give a stabilized fillet liquid;
(c) subjecting the rind to the steps of:
  (i) squeezing to give a crude rind liquid;
  (ii) removing coarse fibers from the crude rind liquid to give a rind liquid;
  (iii) reducing anthraquinone present in the rind liquid to give a rind liquid relatively free of anthraquinone;
  (iv) stabilizing the rind liquid relatively free of anthraquinone to give a stabilized rind liquid; and
(d) combining the stabilized fillet liquid with the stabilized rind liquid.

One embodiment of the present invention is a bifurcated method to process an aloe whole leaf. The method comprises: (a) Cleaning an aloe whole leaf to give a cleaned aloe whole leaf; (b) separating rind from the cleaned aloe whole leaf to produce a fillet. Then separately treat the fillet and the rind. Apart from the rind, the fillet is subjected to the steps of: (i) grinding to give a ground fillet; (ii) removing coarse fibers from the ground fillet to give a relatively fiber-free fillet liquid; (iii) homogenizing the relatively fiber-free fillet liquid to give a homogenized fillet liquid; and (iv) stabilizing the homogenized fillet liquid with a preservative to give a stabilized fillet liquid. Separately, the rind is subjected to the steps of: (i) chopping to give chopped rinds; (ii) adjusting total solid content of the chopped rinds with water to give an adjusted rind solid mixture; (iii) grinding the adjusted total solid mixture to give a ground adjusted rind solid mixture; (iv) removing coarse fibers from the ground adjusted rind solid mixture to give a relatively fiber-free rind liquid; (v) homogenizing the relatively fiber-free rind liquid to give a homogenized rind liquid; (vi) reducing anthraquinone present in the homogenized rind liquid to give a rind liquid relatively free of anthraquinone; (vii) sterilizing the rind liquid relatively free of anthraquinone to give a sterilized rind liquid; and (viii) stabilizing the sterilized rind liquid with a preservative to give a stabilized rind liquid. Then the stabilized fillet liquid is combined with the stabilized rind liquid.

Accordingly, an object of the present invention is to provide a bifurcated method to process an aloe whole leaf.

Another object of the present invention is to provide a bifurcated method to process an aloe whole leaf, whose bifurcated method is capable of preserving most of the bioactive chemical entities naturally present in the aloe whole leaf.

Still another object of the present invention is to provide a method wherein each of the aloe fillet and the aloe rind is first processed separately and the resultant products are eventually combined.

Yet another object of the present invention is to provide aloe products prepared by a whole-leaf bifurcated method, whose products are suitable for making beverages, food additives, and other consumer uses.

Other objects, advantages and novel features of the present invention will become apparent from the following description of the invention.

DESCRIPTION OF THE FIGURE

FIG. 1 shows a sequence of steps utilized in one embodiment of the present invention.

DETAILED DESCRIPTION

The problems discussed above, inherent in the current whole-leaf process, have been solved in the embodiments of the present invention pertains, in one aspect, to a bifurcated method to process an aloe whole leaf. The present invention of the bifurcated whole-leaf process can preserve most of the bioactive chemical entities and components naturally present in the aloe whole leaf.

As used herein, the term "bioactive" means "possessing biological activity," such as a pharmacological or a therapeutic activity. More specifically, the biological activity can be: Analgesic; antiviral; anti-inflammatory; antineoplastic; immune stimulating; immune modulating; adjuvant; or a combination thereof.

A substance has an "analgesic" activity if it can relief pain.

An "antiviral" activity is the activity of a substance that can interfere directly or indirectly with the replication of a virion or its infection and/or interaction with a host cell.

A substance has an "anti-inflammatory" activity if the substance can inhibit the inflammatory process of heat, redness, swelling, pain and loss of function as a result of tissue destructive processes and response.

An "antineoplastic" activity is the activity of a substance that can interfere with the cell cycle of tumor cells, that can prevent replication or repair of tumor cells, or that can increase programmed cell death or apoptosis, and/or effect the immunogenicity of tumor cells resulting in their destruction.

A substance has an "immune stimulating" activity if the substance can stimulate the immune system by either promoting cytokine release from macrophages, increase specific, or non-specific, phagocytosis, and/or stimulate directly or indirectly the components of the host defense system.

A substance has an "immune modulating" activity if the substance can interact with the immune system to either up-regulate (enhance) or down-regulate (lessen) the immune response.

A substance has an "adjuvant" activity if the substance can enhance, non-specifically, the immune response to an antigen. A substance is also known to have an "adjuvant" activity if the substance, when added, can assist a drug in a formulation to hasten or increase the action of the principal ingredient of the drug.

The bioactive chemical entities or components can be one or more chemical substances, or mixtures of different chemical substances, which chemical substances or mixtures thereof possess biological activity or activities. Such chemical substances could include a moiety such as an organic acid, protein, amino acid, carbohydrate, peptide, glycoprotein, sterol, other organic/inorganic substances, and mixtures thereof.

The word "bifurcated" is used to denote that each of the aloe fillet and the aloe rind is first processed separately.

Aloe gel fillet that is substantially anthraquinone-free can be produced by the following steps from a leaf of an aloe plant:

1. Washing the aloe leaf in a bactericidal solution to remove substantially all surface dirt and bacteria;
2. removing at least a first end portion from the washed leaf;
3. draining, preserving and collecting anthraquinone rich sap from the cut and washed leaf; and
4. removing rind from the leaf to produce a substantially anthraquinone-free gel fillet.

Aloe raw gel, "raw gel," or "aloe juice" that is substantially anthraquinone-free having solubilized and suspended matter can be obtained by grinding and homogenizing the substantially anthraquinone-free aloe gel fillet.

Each of the different methods set forth above uses the aloe fillet only. Invariably, the rind is discarded before processing.

The present invention, however, pertains to a bifurcated method to process the aloe whole leaf. In the present invention, the rind is not discarded. Rather, the rind is separately processed to yield a liquid rind product. The fillet is also separately processed which yields a liquid fillet product. The liquid rind product and the liquid fillet product are then combined for further use, such as for beverages, food additives, cosmetic, and others. The bifurcated method to process the aloe whole leaf help to preserve and retain most of the bioactive chemical entities and components naturally present in the aloe whole leaf.

Broadly, one embodiment of the present invention pertains to a bifurcated method for processing an aloe whole leaf comprising:

(a) washing the aloe whole leaf to give a cleaned aloe whole leaf;
(b) separating rind from the cleaned aloe whole leaf to produce a fillet;
(c) subjecting the fillet to the steps of:
   (i) grinding to give a ground fillet;
   (ii) removing coarse fibers from the ground fillet to give a relatively fiber-free fillet liquid;
   (iii) homogenizing the relatively fiber-free fillet liquid to give a homogenized fillet liquid;
   (iv) stabilizing the homogenized fillet liquid with a preservative to give a stabilized fillet liquid;
(d) subjecting the rind to the steps of:
   (i) chopping to give chopped rinds;
   (ii) adjusting total solid content of the chopped rinds with water to give an adjusted rind solid mixture;
   (iii) grinding the adjusted total solid mixture to give a ground adjusted rind solid mixture;
   (iv) removing coarse fibers from the ground adjusted rind solid mixture to give a relatively fiber-free rind liquid;
   (v) homogenizing the relatively fiber-free rind liquid to give a homogenized rind liquid;
   (vi) reducing anthraquinone present in the homogenized rind liquid to give a rind liquid relatively free of anthraquinone;
   (vii) sterilizing the rind liquid relatively free of anthraquinone to give a sterilized rind liquid;
   (viii) stabilizing the sterilized rind liquid with a preservative to give a stabilized rind liquid; and
(e) combining the stabilized fillet liquid with the stabilized rind liquid.

FIG. 1 shows one embodiment of the present invention and it involves the following steps:

1.—Whole Aloe Leaves

Aloe vera leaves arrive from the farm are soaked in water and rinsed with high pressure water jets to remove dirt and other foreign materials.

2.—Chlorinated Water Soak

Aloe vera leaves are then placed in a water flume having water that typically contains about 200 ppm chlorine. Typical residence time is about 30 minutes.

3.—Wash Operation

As leaves enter the processing plant, they are sprayed with water to remove excess chlorine water.

4.—Filleting Operation

Rind, thorns, tips and bases of the aloe leaves are removed, preferably manually, leaving two products: (1) The aloe vera fillets (about 30–50% w/w); and (2) rinds, tips, bases and thorns, collected together and hereinafter called "rind."

5.—Water Rinse

At this step, the incoming material is rinsed with clean water to remove residue chlorine and other 6.—Chopping Operation where the rinds are grounded by a cutting-action machine. The machine used here is constructed of food grade stainless steel and after the material passes through this step, is size is reduced to from about 0.1 mm to about 15 mm in size, preferably from about 0.1 mm to about 5 mm in size, and more preferably from about 0.2 mm to about 1 mm in size.

7.—Total Solid Adjustment

At this step, aqueous liquid is added if needed to adjust the total solid content. The total solid content, as expressed by the refractive index, must be in a range from about 1.2500 to about 1.4500, preferably from about 1.3000 to about 1.4000, more preferably from about 1.3200 to about 1.3500, and even more preferably from about 1.3350 to about 1.3355.

8.—Course Grinding Operation

At this step, the rind fraction is grounded further to yield a mixture of chunks having particle size smaller than about 2 mm, and more preferably smaller than about 1 mm.

9.—Fiber Removal Operation

At this step, the rinds fraction undergoes a coarse filtration with a maximum particle size of about 500 mm. The solid cake, the plant fiber, is discarded and the filtrate liquid is used for the subsequent steps.

10.—Homogenization Step

Here the liquid is passed through a metal mesh (about 5 micrometers) at high pressure (about 1500 psi) to break any aggregates that occur in the aloe vera liquid. the purpose of this step is to reduce the viscosity of the liquid by mechanical means while preserving the chemical integrity of the liquid.

11.—Anthraquinone Reduction Step

The resulting liquid is treated with activated charcoal, preferably granulated with average particle size of about 1.5 mm. The liquid and the activated charcoal mixture is then stirred for a period of time, usually aobut 10 minutes. The amount of activated charcoal used ranges from about 0.5 to about 3 kgs per about 400 liters of aloe rind liquid.

12.—Filtration Step

At this step, the mixture of aloe rind liquid and activated charcoal is filtered using a #2 standard filter bags with pore size of about 300–50 um. the preferred pore size is aobut 100 um. then the resulting filtered liquid is passed through a second filtration step using bags with a pore size of about 50–5 um. The preferred pore size is about 10 um. A filter press could also be used utilizing the same rages of particle sizes.

13.—HTST Sterilization Step

The liquid is then pumped through a high temperature short time sterilizer ("HTST") which elevates the temperature of the fluid to about 100 degrees C. The liquid is kept at this temperature for about 30 seconds, then cooled to about 20 degrees C. The cycle is repeated 2 to 5 times, but a single cycle can be sufficient.

14.—Stabilization Step

At this point, a preservative or a mixture of preservatives is added to the liquid. Examples of preservatives include sodium benzoate, potassium sorbate, citric acid, and Vitamin E. Preferably, a mixture of about 0.08% of sodium benzoate and about 0.15% of citric acid is used, the citric acid used is enough to stabilize the pH at about 3.4.

Further, the amount of water from the combined stabilized fillet liquid and stabilized rind liquid can be reduce to yield a syrup or even freeze dried to produce a powder.

The resultant product can be used for beverages, food additives, cosmetics, and others. Flavoring agents that can be used include vanilla, cinnamon oil, and others.

Various modifications of the disclosed processes to produce whole leaf aloe products, as well as alternative modifications, variations and equivalents will become apparent to persons skilled in the art upon reading the above general description of the preferred embodiment. The foregoing general description is not intended to limit the scope of the appended claims, which cover any such modifications, equivalents or variations.

What is claimed is:

1. A method for precessing an aloe whole leaf comprising:
   (a) separating rind and fillet from a cleaned aloe whole leaf;
   (b) subjecting said fillet to the steps of:
      (i) squeezing to give a crude fillet liquid;
      (ii) removing coarse fibers from said crude fillet liquid to give a fillet liquid;
      (iii) stabilizing said fillet liquid with a preservative to give a stabilized fillet liquid;
   (c) subjecting said rind to the steps of:
      (i) squeezing to give a crude rind liquid;
      (ii) removing coarse fibers from said crude rind liquid to give a rind liquid;
      (iii) reducing anthraquinone present in said rind liquid to give a rind liquid with a reduced anthraquinone content;
      (iv) stabilizing said rind liquid relatively free of anthraquinone to give a stabilized rind liquid; and
   (d) combining said stabilized fillet liquid with said stabilized rind liquid.

2. The method of claim 1, wherein said aloe whole leaf is cleaned by washing in water.

3. The method of claim 1, wherein said coarse fibers are removed from said crude fillet liquid by filtration.

4. The method of claim 1, wherein said anthraquinone present in said rind liquid is reduced by treating with charcoal.

5. The method of claim 1, wherein said fillet liquid is stabilized by the addition of a preservative.

6. The method of claim 1 further comprising the step of chopping said rind before the step of squeezing said rind.

7. The method of claim 6 further comprising the step of adjusting total solid content of said chopped rind before the step of squeezing said rind.

8. The method of claim 1 further comprising the step of high temperature short time sterilization before the step of stabilizing said rind liquid with a reduced anthraquinone content.

9. A method for processing an aloe whole leaf comprising:
   (a) cleaning said aloe whole leaf to give a cleaned aloe whole leaf;
   (b) separating rind from said cleaned aloe whole leaf to produce a fillet;
   (c) subjecting said fillet to the steps of:
      (i) grinding to give a ground fillet;
      (ii) removing coarse fibers from said ground fillet to give a fillet liquid with a reduced fiber content;
      (iii) homogenizing said fillet liquid with a reduced fiber content to give a homogenized fillet liquid;
      (iv) stabilizing said homogenized fillet liquid with a preservative to give a stabilized fillet liquid;
   (d) subjecting said rind to the steps of:
      (i) chopping to give chopped rinds;
      (ii) adjusting total solid content of said chopped rinds with water to give an adjusted rind solid mixture;
      (iii) grinding said adjusted total solid mixture to give a ground adjusted rind solid mixture;
      (iv) removing coarse fibers from said ground adjusted rind solid mixture to five a rind liquid with a reduced fiber content;
      (v) homogenizing said rind liquid with a reduced fiber content to give a homogenized rind liquid;
      (vi) reducing anthraquinone present in said homogenized rind liquid to give a rind liquid with a reduced anthraquinone content;
      (vii) sterilizing said rind liquid with a reduced anthraquinone content to give a sterilized rind liquid;
      (viii) stabilizing said sterilized rind liquid with a preservative to give a stabilized rind liquid; and
   (e) combining said stabilized fillet liquid with said stabilized rind liquid.

10. The method of claim 9, wherein said cleaning of said aloe whole leaf is accomplished by washing with water.

11. The method of claim 9, wherein said grinding of said fillet gives a ground fillet of less than about 2 mm in size.

12. The method of claim 9, wherein said coarse fibers are removed from said crude fillet liquid by filtration.

13. The method of claim 9, wherein said fillet liquid with a reduced fiber content is homogenized by passing through a metal mesh of about 5 µm at a pressure of about 1500 psi.

14. The method of claim 9, wherein said fillet liquid is stabilized by the addition of a preservative.

15. The method of claim 9, wherein said chopped rinds have a size of from about 0.1 mm to about 5 mm.

16. The method of claim 9, wherein said adjusted rind solid mixture has a refractive index of from about 1.3200 to about 1.3500.

17. The method of claim 9, wherein said coarse fibers are removed from said ground adjusted rind solid mixture by filtration.

18. The method of claim 9, wherein said rind liquid with a reduced fiber content is homogenized by passing through a metal mesh of about 5 µm at a pressure of about 1500 psi.

19. The method of claim 9, wherein said anthraquinone present in said rind liquid is reduced by treating with charcoal.

20. The method of claim 9, wherein said rind liquid with a reduced anthraquinone content of anthraquinone is sterilized by high temperature short time sterilization.

21. The method of claim 9, wherein said sterilized rind liquid is stabilized by the addition of a preservative.

22. A method for processing an aloe whole leaf comprising:
   (a) cleaning said aloe whole leaf with water to give a cleaned aloe whole leaf;
   (b) separating rind from said cleaned aloe whole leaf to produce a fillet;
   (c) subjecting said fillet to the steps of:
      (i) grinding to give a ground fillet having a size of less than about 2 mm;
      (ii) filtering said ground fillet to remove coarse fibers to give a fillet liquid with a reduced fiber content;
      (iii) passing said fillet liquid with a reduced fiber content through a metal mesh of about 5 µm at a pressure of about 1500 psi to give a homogenized fillet liquid;
      (iv) stabilizing said homogenized fillet liquid with a mixture of sodium benzoate and citric acid to give a stabilized fillet liquid;
   (d) subjecting said rind to the steps of:
      (i) chopping to give chopped rinds having sized from about 0.2 mm to about 1 mm;
      (ii) adjusting total solid content of said chopped rinds with water to give an adjusted rind solid mixture having a refractive index of from about 1.3350 to about 1.3355;
      (iii) grinding said adjusted total solid mixture to give a ground adjusted rind solid mixture with particle size smaller than about 1 mm;
      (iv) removing coarse fibers from said ground adjusted rind solid mixture to give a rind liquid with a reduced fiber content;
      (v) passing said rind liquid with a reduced fiber content through a metal mesh of about 5 µm at a pressure of about 1500 psi to give a homogenized rind liquid;
      (vi) treating said homogenized rind liquid with charcoal to give a rind liquid with a reduced anthraquinone content;
      (vii) sterilizing said rind liquid with a reduced anthraquinone content under about 100 degrees C. for about 30 seconds to give a sterilized rind liquid;
      (viii) stabilizing said sterilized rind liquid with a mixture of sodium benzoate and citric acid to give a stabilized rind liquid; and
   (e) combining said stabilized fillet liquid with said stabilized rind liquid.

* * * * *

UNITED STATES PATENT AND TRADEMARK OFFICE
CERTIFICATE OF CORRECTION

PATENT NO. : 5,925,357
DATED : July 20, 1999
INVENTOR(S) : Luiz Cerqueira, et al.

It is certified that error appears in the above-identified patent and that said Letters Patent is hereby corrected as shown below:

| | |
|---|---|
| Col. 6, line 47 | add - - contaminates. - - |
| Col. 6, line 52 | "is" should be - - its - - |
| Col. 7, line 9 | 'the" should be - - The - - |
| Col. 7, line 17 | "aobut" should be - - about - - |
| Col. 7, line 23 | "the" should be - - The - - |
| Col. 7, line 23 | "aobut" should be - - about - - |
| Col. 7, line 24 | "then" should be - - Then - - |
| Col. 7, line 27 | "rages" should be - - ranges - - |
| Col. 7, line 44 | "reduce" should be - - reduced - - |
| Col. 7, line 58 | "precessing" should be - - processing - - |
| Col. 8, line 49 | "five" should be - - give - - |

Signed and Sealed this

Fifteenth Day of August, 2000

Attest:

Q. TODD DICKINSON

*Attesting Officer*     *Director of Patents and Trademarks*